United States Patent
Hoggarth et al.

(10) Patent No.: US 12,059,323 B2
(45) Date of Patent: Aug. 13, 2024

(54) WOUND DRESSING

(71) Applicant: Medtrade Products Limited, Crewe (GB)

(72) Inventors: Andrew Hoggarth, Cheshire (GB); Craig Hardy, Cardiagan (GB); Matthew Grist, Nantwich (GB)

(73) Assignee: Medtrade Products Limited, Crewe (GB)

( * ) Notice: Subject to any disclaimer, the term of this patent is extended or adjusted under 35 U.S.C. 154(b) by 675 days.

(21) Appl. No.: 16/639,960

(22) PCT Filed: Aug. 20, 2018

(86) PCT No.: PCT/GB2018/052350
§ 371 (c)(1),
(2) Date: Feb. 18, 2020

(87) PCT Pub. No.: WO2019/034896
PCT Pub. Date: Feb. 21, 2019

(65) Prior Publication Data
US 2020/0246192 A1    Aug. 6, 2020

(30) Foreign Application Priority Data
Aug. 18, 2017  (GB) ..................................... 1713272

(51) Int. Cl.
*A61F 13/02* (2024.01)
*A61F 13/00* (2024.01)
(Continued)

(52) U.S. Cl.
CPC ........ *A61F 13/023* (2013.01); *A61F 13/0253* (2013.01); *A61F 13/0263* (2013.01);
(Continued)

(58) Field of Classification Search
CPC ................ A61F 13/00; A61F 13/00021; A61F 13/00085; A61F 13/023; A61F 13/024;
(Continued)

(56) References Cited

U.S. PATENT DOCUMENTS

| | | | |
|---|---|---|---|
| 5,431,633 A * | 7/1995 | Fury | A61M 39/0247 |
| | | | 604/122 |
| 10,639,207 B1 * | 5/2020 | Harder | A61F 13/025 |

(Continued)

FOREIGN PATENT DOCUMENTS

| | | |
|---|---|---|
| EP | 0392640 | 7/1991 |
| EP | 0538917 | 4/1993 |

(Continued)

*Primary Examiner* — Caitlin A Carreiro
(74) *Attorney, Agent, or Firm* — Burns & Levinson LLP; Daniel J. McGrath

(57) ABSTRACT

Wound dressings for use in cases of a patient suffering a penetrating chest trauma. The wound dressing includes a base layer having a lower surface facing the wound and an upper surface facing away from the wound, and an aperture therethrough for locating over the wound, and a top layer extending over the aperture and at least a part of the upper surface. The base layer is connected to the top layer such that the wound dressing can transition from an open configuration in which the aperture and an area external to the wound dressing are in fluid communication via at least one opening at a perimeter between the base layer and the top layer, to a closed configuration in which the top layer forms a seal over the aperture.

24 Claims, 8 Drawing Sheets

Figure 1:
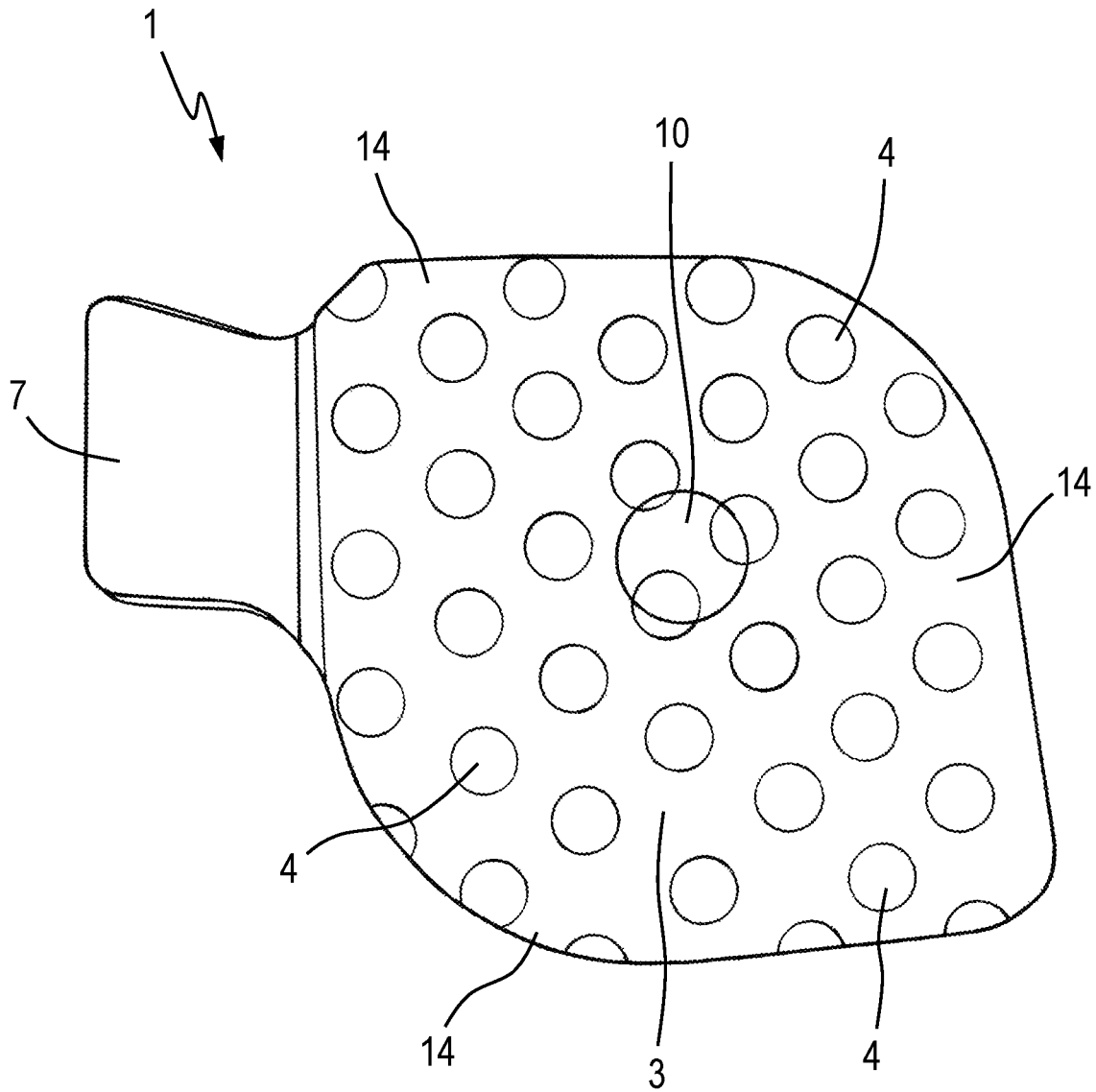

(51) Int. Cl.
*A61F 13/0246* (2024.01)
*A61L 15/16* (2006.01)

(52) U.S. Cl.
CPC .......... *A61F 13/0266* (2013.01); *A61L 15/16* (2013.01); *A61F 2013/00114* (2013.01); *A61F 2013/00251* (2013.01); *A61L 2300/42* (2013.01)

(58) Field of Classification Search
CPC .............. A61F 13/0243; A61F 13/0253; A61F 13/0263; A61F 13/0266; A61F 13/0246; A61F 13/0259; A61F 13/60; A61F 2013/00114; A61F 2013/00246; A61F 2013/00251; A61F 2013/00582; A61F 2013/00089; A61L 15/16; A61L 15/008; A61L 2300/42
USPC ...... 602/41–43, 47, 52, 57–59, 54; 128/853, 128/854, 887–890
See application file for complete search history.

(56) References Cited

U.S. PATENT DOCUMENTS

| | | | | |
|---|---|---|---|---|
| 2011/0106030 | A1* | 5/2011 | Scholz | A61M 27/00 604/319 |
| 2011/0282309 | A1* | 11/2011 | Adie | A61F 13/022 604/319 |
| 2013/0030342 | A1* | 1/2013 | Scheremet | A61M 1/04 602/54 |
| 2014/0288477 | A1 | 9/2014 | Shulman et al. | |
| 2015/0320919 | A1* | 11/2015 | Bussett | A61M 1/04 604/540 |

FOREIGN PATENT DOCUMENTS

| | | |
|---|---|---|
| EP | 2422757 | 2/2012 |
| GB | 2423718 | 9/2006 |
| WO | 2007/040615 | 4/2007 |
| WO | 2015/059501 | 4/2015 |

* cited by examiner

WOUND DRESSING

CROSS-REFERENCE TO RELATED APPLICATIONS

This application is the U.S. national phase entry under 35 U.S.C. § 371 of International Application No. PCT/GB2018/052350, filed Aug. 20, 2018, entitled WOUND DRESSING, which in turn claims priority to and benefit of Great Britain Application No. 1713272.1, filed Aug. 18, 2017, each of which is incorporated herein by reference in their entirety for all purposes.

TECHNICAL FIELD OF THE INVENTION

The present invention relates to wound dressings. More particularly, the present invention relates to wound dressings for use in cases of a patient suffering a penetrating chest trauma.

BACKGROUND TO THE INVENTION

An open chest wound can refer to a wound in the chest wall that enters the lung cavity. Penetrating chest injuries can be caused by an object, such as a bullet, a piece of shrapnel or a knife, entering the chest of a human or animal body and penetrating the chest wall. Individuals at risk of incurring penetrating chest injuries include those who handle weapons, such as law enforcement officers, military personnel, and other professions that present a risk of sustaining open chest wounds.

There are various conditions that can result from a penetrating chest injury, including tension pneumothorax, open pneumothorax, and haemothorax.

In tension pneumothorax, air enters the pleural cavity of the patient's lung and is not expelled by exhaling and becomes trapped.

An open pneumothorax occurs when air is drawn into an open chest wound and accumulates in the chest cavity. The trapped air builds up pressure in the chest and, if untreated, can cause the affected side of the lung to collapse.

In haemothorax, blood enters into the pleural cavity of the patient's lung. The fluid in the lungs can interfere with normal breathing by limiting the expansion of the lungs. If left untreated, the blood accumulation can put pressure on the mediastinum and the trachea, effectively limiting the amount that the heart's ventricles are able to fill.

It is therefore important to administer treatment to a patient suffering a penetrating chest wound as soon as possible. The initial treatment typically requires the application of a device that provides an outlet for bodily fluid, such as blood, and air from the pleural space of the lungs but prevents the ingress of air and fluid into the pleural space through the wound.

Wound dressings have been prepared to address the aforementioned issues.

One such dressing described in EP 2433596 comprises a multilayer sheet member comprising a first layer comprising an aperture that would encircle the wound, a second layer of a backing material overlain over the first layer containing a corresponding aperture, a third layer with a corresponding aperture overlain over the second layer providing an anchor layer for a fourth layer of thin flexible material to serve as the moveable portion of a plurality of flutter valves, the fourth layer having no corresponding aperture but a plurality of holes at its periphery. The holes serve as the flutter valves and the fourth layer is sealed around its periphery by a seal line. However, a disadvantage of the prior art is that, in use, the flutter valves may become blocked with blood, leading to a decrease in the ability of the dressing to provide an outlet for air and bodily fluid. Also, due to the number of layers present, the dressing can be bulky which is a disadvantage for military personnel who may require the dressing to be worn under body armour, for example.

The present invention has been developed with the aforementioned problems in mind.

SUMMARY OF THE INVENTION

According to a first aspect of the present invention, there is provided a wound dressing comprising:
  a base layer having a lower surface facing the wound and an upper surface facing away from the wound, and an aperture therethrough for locating over the wound; and
  a top layer extending over the aperture and at least a part of the upper surface,
  wherein the base layer is connected to the top layer such that the wound dressing can transition from an open configuration in which the aperture and an area external to the wound dressing are in fluid communication via at least one opening at a perimeter between the base layer and the top layer, to a closed configuration in which the top layer forms a seal over the aperture.

Unless otherwise stated, reference herein to fluid is intended to refer both to air and to bodily fluid, including blood, plasma and the like.

The wound dressing of the present invention may be applied to a patient suffering from a penetrating chest wound. The wound dressing can effectively act as a one-way valve, allowing for the flow of fluid from a patient away from the wound whilst preventing the ingress of fluid into the wound and the chest cavity. This is beneficial for assisting in the prevention of tension pneumothorax, open pneumothorax, and haemothorax and the consequences thereof. Furthermore, given the structure of the wound dressing of the present invention, it has a low profile, making it suitable for application to a patient underneath body armour and the like.

The top layer may be connected to the base layer by at least one supporting structure. Preferably, the top layer is connected to the base layer by a plurality of supporting structures. The supporting structures may be spaced apart. Preferably, the supporting structures are evenly spaced apart.

Alternatively, the top layer may be sealed directly to the base layer. In such an embodiment, the top layer may be connected to the base layer by heat sealing, including ultrasonic welding or the like. In such embodiments, heat sealing typically involves the localised application of heat and optionally pressure to the top and base layers. Preferably, the top and base layers are held together followed by the localised application of heat. Ultrasonic welding typically involves the localised application of ultrasonic acoustic vibrations to the top and base layers being held together. The ultrasound generates heat in the locality of application, causing the two layers to melt together. The two layers may be clamped together, one of the clamps being a sonotrode to apply the ultrasound.

The top layer may be sealed to the base layer by applying heat and optionally pressure to melt the two layers together.

It is envisaged that the top layer and the base layer may be connected together by sealing at one or more locations. This may be achieved by the localised application of heat or ultrasound and optionally pressure to the top layer and base layer at the one or more locations to seal the two layers together.

When in the open configuration, the wound dressing may comprise an open region between the aperture and the at least one opening at the perimeter. When in the closed configuration, the top layer has collapsed against the base layer and optionally around the supporting structure(s), thus substantially closing the open region between the aperture and the at least one opening at the perimeter.

In the open configuration, fluid may flow around the at least one supporting structure in the open region. Where there is a plurality of supporting structures, the fluid may flow around the supporting structures in the open region.

In some embodiments, the top layer is connected to the base layer by at least two supporting structures, preferably at least five supporting structures, more preferably at least ten supporting structures, even more preferably at least twenty supporting structures and most preferably at least thirty supporting structures.

The at least one supporting structure may comprise an island, a wall, or the like. The island, wall, or the like may comprise a regular or irregular shape. For example, the supporting structure(s) may comprise a substantially circular cross-section, a substantially rectangular cross-section or, where there is a plurality of supporting structures there may be a mixture of supporting structures comprising substantially circular and substantially rectangular cross-sections.

Preferably, the supporting structure comprises an island. More preferably, the at least one supporting structure comprises a plurality of islands.

The supporting structures may be spaced apart islands. Preferably, the islands are substantially evenly spaced apart.

The spaced apart islands may extend toward the perimeter of the wound dressing.

The perimeter between the base layer and the top layer may comprise a plurality of openings.

The supporting structure(s) at the perimeter may be incomplete or have a cut-away section. This may result from the manufacturing process where the wound dressing is cut from a larger structure, the cutting process dissecting one or more of the supporting structure(s).

The perimeter of the wound dressing may comprise intermittent openings. The intermittent openings may be formed between two adjacent supporting structures, such as two adjacent islands or portions of islands.

The supporting structures may create a series of passageways for fluid to flow down or around as it passes from the wound site and out through an opening into an area external to the wound dressing. Where the supporting structure comprises one or more islands, the fluid may flow around the islands as it passes through the open region.

The open configuration of the wound dressing may be adopted when the pressure in the pleural cavity is too high. This can arise during expiration by the patient, which creates a pressure increase in the pleural cavity. When the pressure in the pleural cavity is too high, the top layer is forced away from the upper surface of the base layer creating an open region from the aperture surrounding the wound to an area external to the wound dressing. This enables the passage of fluid out from the pleural cavity and a release of pressure.

The closed configuration of the wound dressing may be adopted when the pressure in the pleural cavity is decreased. This can arise during inhalation by the patient, which creates a pressure decrease in the pleural cavity. When the pressure in the pleural cavity is decreased, the top layer is forced against the upper surface of the base layer and optionally around the supporting structure(s), closing the open region and forming an airtight seal over the aperture. This prevents the ingress of fluid from an area external to the wound, such as air, into the wound and pleural cavity.

The supporting structure(s) may be made from an adhesive material. In such embodiments, the adhesive supporting structure(s) connect the base layer to the top layer.

Thus, the base layer and the top layer may be connected by a plurality of adhesive islands. In such embodiments, the adhesive islands serve to adhere the top layer to the base layer.

Preferably, the adhesive for the supporting structure(s) does not delaminate under moist or wet conditions and is suitable to maintain adherence to the top layer and base layer under fluctuations in pressure. Suitable adhesives include, but are not limited to, polyurethane based adhesives, acrylic based adhesives, silicone based adhesives, and hydrogels, such as for example a synthetic rubber hydrogel.

Alternatively, a thermoplastic adhesive such as a hot melt adhesive would be suitable. In such embodiments, a thermoplastic adhesive is melted, typically using a hot glue gun, and applied to the base and/or the top layer, after which it solidifies over a period of time. Typically, the time for the adhesive to solidify is up to around one minute. The melting temperature of the thermoplastic adhesive is typically from 120 to 210° C. Suitable examples of thermoplastic adhesives include those sold under the trade name Schaetti adhesive.

The supporting structure(s) may overlap a portion, but not all, of the aperture.

Thus, one or more islands may overlap the aperture. In such instances, only a portion of the island will be connected to the upper surface of the base layer.

Additionally, or alternatively, one or more islands may be wholly located within the area of the aperture. In such instances, the subject islands will be connected to the top layer but not the base layer.

The supporting structure(s) may form an ordered pattern between the base and top layers. For example, the pattern may comprise a symmetrical repeating pattern of adjacent rows of islands.

In one embodiment, the supporting structure(s) are formed by the application of adhesive to the base layer and/or the top layer. The adhesive may be applied in one or more locations onto the upper surface of the base layer and/or the lower surface of the top layer. The supporting structures may comprise islands of adhesive that have been applied to the upper surface of the base layer and/or the lower surface of the top layer.

In another embodiment, the wound dressing may further comprise a means for providing one or more supporting structures located between the top layer and the base layer, wherein at least a portion of the upper surface of the base layer and/or the lower surface of the top layer comprises an adhesive. Suitable adhesives include any of the adhesives referred to herein for the supporting structures.

The means for providing one or more supporting structures may comprise a perforated layer. The perforated layer may comprise a lower surface facing the wound and an upper surface facing away from the wound and an aperture therethrough which overlaps with the aperture in the base layer. Preferably, the aperture in the perforated layer corresponds to the aperture in the base layer. The perforated layer further comprises at least one perforation therethrough in addition to the aperture.

In such an embodiment, the supporting structure(s) are formed when the top layer, base layer and perforated layer are brought together. The adhesive on the base layer and/or the top layer may connect the top layer to the base layer through the perforations in the perforated layer. The perforations in the perforated layer effectively provide windows through which the adhesive on the upper surface of the base layer can adhere to the top layer and/or the adhesive on the lower surface of the top layer can adhere to the base layer. In such embodiments, the supporting structures comprise islands of adhesive connecting the base layer to the top layer.

Preferably, the adhesive is on the upper surface of the base layer. The adhesive may be applied to all or part of the upper surface of the base layer. Preferably, the adhesive is applied to all of the upper surface of the base layer. The base layer may comprise adhesive on all or part of both its upper surface and lower surface. The base layer may comprise adhesive on substantially all of both its upper surface and lower surface. The base layer may comprise a double-sided film. The base layer may comprise a double-sided tape.

The perforated layer may comprise a plurality of perforations therethrough. The perforations may be arranged in a radial pattern extending outwardly from the aperture. The pattern may comprise a circumferential arrangement of perforations around the aperture. The pattern may comprise a plurality of circumferential arrangements of perforations around the aperture, radially extending outwardly from the aperture.

The pattern may comprise a staggered arrangement of perforations. The perforations in one circumferential arrangement may be staggered relative to the perforations in the adjacent circumferential arrangement. Beneficially, a staggered arrangement of perforations avoids the potential creation of a channel between the base layer and the top layer that would run directly from the aperture to the edge of the wound dressing. It is desirable to avoid such a channel forming as this can prevent the wound dressing from acting as a valve, particularly in situations where the wound dressing is applied to a concave surface on the patient.

In such an embodiment, when in the closed configuration, the top layer has collapsed against the perforated layer, thus substantially closing the open region between the aperture and the at least one opening at the perimeter.

The base layer may be in the form of a film, a sheet or a textile. The base layer may be occlusive.

The base layer may be a flexible material. Beneficially, this enables the base layer to conform to a patient's skin. The base layer may comprise, but is not limited to, polyethylene (PE), polyethylene terephthalate (PET), polyurethane (PU), polypropylene (PP), nylon and polyvinylchloride (PVC) or combinations of two or more of the aforesaid. The base layer may comprise a woven or non-woven textile material. The non-woven textile material may be dry-laid, wet-laid, melt blown, or spun laid. The base layer may alternatively comprise a knitted fabric. Preferably, the base layer comprises a polyethylene film.

The top layer may be in the form of a film. The top layer may comprise a circular film. The top layer may have a smaller surface area than the other layers forming the wound dressing, including the base layer and/or the perforated layer. In such embodiments, the top layer may not extend to the edge of the other layers forming the wound dressing.

The top layer may be occlusive. The top layer may be flexible.

The top layer may be a flexible material. Furthermore, the top layer may be sufficiently strong to withstand fluctuations in pressure resulting from the breathing of the patient. The top layer may comprise, but is not limited to, polyethylene (PE), polyethylene terephthalate (PET), polyurethane (PU), polypropylene (PP), nylon and polyvinylchloride (PVC) or combinations of two or more of the aforesaid. Preferably, the top layer comprises polyurethane. A suitable polyurethane film may have a thickness of less than or equal to 60 microns, a tensile strength of at least 2000 g/2.5 cm and/or at least 450% elongation.

Preferably, the base layer and/or the top layer are occlusive or substantially occlusive. By substantially occlusive, it is meant that the layer may have a degree of air permeability but in relation to the action of breathing is effectively occlusive.

In use, the top layer collapses against the upper surface of the base layer sealing the aperture during inspiration and extends outwardly away from the upper surface of the base layer during expiration if the pressure in the pleural cavity is too high.

In embodiments comprising a means for providing one or more supporting structures, such as for example a perforated layer, where the adhesive is on the upper surface of the base layer, the top layer collapses against the upper surface of the perforated layer. Where the adhesive is on the lower surface of the top layer, the lower surface of the perforated layer collapses against the upper surface of the base layer.

Preferably, the base layer adheres to the patient's skin. At least a portion of the lower surface of the base layer may comprise an adhesive. The adhesive may be present on all or part of the lower surface of the base layer. The adhesive may be applied to all or part of the lower surface of the base layer.

The adhesive may be any physiologically acceptable adhesive, such as an adhesive suitable for skin contact without causing irritation. Suitable adhesives include acrylic-based adhesives and silicone-based adhesives.

In some embodiments, the wound dressing may comprise a skin-contact layer. The skin-contact layer may comprise a lower surface facing the wound and an upper surface facing away from the wound. Typically, the upper surface of the skin-contact layer is adhered to the lower surface of the base layer.

The skin-contact layer comprises an aperture therethrough that overlaps with the aperture in the base layer. Preferably, the aperture in the skin-contact layer corresponds to the aperture in the base layer.

The skin-contact layer may comprise an adhesive for adhering the wound dressing to the patient's skin. The adhesive may comprise an acrylic-based adhesive, a silicone adhesive or an adhesive gel, such as a hydrogel, or combinations of two or more of the aforesaid.

The adhesive gel may comprise any self-supporting, flexible substance in gel form. The gel may comprise one or more polymers. The polymers may be synthetic polymers. The polymers may be polysaccharide polymers. The polymers may be cured by UV light, electron beam or thermally cured. The gel may comprise water.

Preferably, the skin-contact layer comprises a hydrogel. Hydrogels are beneficial as they display superior adhesion to wet, soiled or bloody skin. In some embodiments, the gel may have a scrim or supportive mesh contained therein.

The wound care device may comprise a removeable protecting layer. The removeable protecting layer may be located on the lower surface of the skin-contact layer or, in the absence of a skin-contact layer, the lower surface of the base layer.

The removeable protecting layer may serve to protect the lower surface of the skin-contact layer or base layer until the wound dressing is ready for application. At that time, the removeable protecting layer may be peeled off the lower surface of the skin-contact layer or base layer.

The removeable protecting layer may be a flexible material. The removeable protecting layer may comprise, but is not limited to, polyethylene terephthalate (PET), siliconized paper, and the like.

The wound dressing may comprise a tab for ease of application of the wound dressing to the patient. For example, the tab provides for ease of separation of the removable protecting layer from the base layer or skin-contact layer. Further, the tab is also advantageous for so called 'burping' the patient, which involves the lifting of the tab whilst the wound dressing is in place to release excess pressure.

The tab may be located at an edge of the wound dressing. The tab may be formed by an extended portion of the top layer and/or the base layer. Preferably, the tab is formed by an extended portion of the base layer.

The tab may further comprise at least one supporting layer located on or between the extended portion of the base layer and/or the top layer. The supporting layer may comprise, but is not limited to, polyethylene, polypropylene, polyethylene terephthalate, or combinations of two or more of the aforesaid. The supporting layer may be a woven or non-woven material.

The tab may comprise two or more supporting layers.

The wound dressing may further comprise an active pharmaceutical ingredient, an anticoagulant, or a combination thereof. Any one or more of the top layer, the base layer, the skin-contact layer, supporting structure(s), the means for providing one or more supporting structures, tab and/or any other component of the wound dressing may further comprise the active pharmaceutical ingredient, the anticoagulant or the combination thereof. Beneficially, this may assist in the functioning of the wound dressing by preventing clotting within the open region which could cause blockages.

The active pharmaceutical ingredient, the anticoagulant, or the combination thereof may be at least partially coated onto, or contained in, the top layer, the base layer, the skin-contact layer, supporting structure(s), the means for providing one or more supporting structures, tab and/or any other component of the wound dressing. The top layer, the base layer, the skin-contact layer, the means for providing one or more supporting structures or the tab may be partially or fully coated with the active pharmaceutical ingredient, the anticoagulant, or the combination thereof.

According to a second aspect of the present invention, there is provided a wound dressing as described herein for application to a penetrating chest wound.

There is also provided a method of treating a penetrating chest wound, the method comprising the step of applying to a penetrating chest wound a wound dressing as described herein.

According to a third aspect of the present invention, there is provided a method of manufacturing a wound dressing as described herein, the method comprising connecting a base layer to a top layer.

The method of manufacturing a wound dressing may comprise connecting a base layer having a lower surface facing the wound and an upper surface facing away from the wound, and an aperture therethrough for locating over the wound to a top layer extending over the aperture and at least a part of the upper surface, wherein the base layer is connected to the top layer such that the wound dressing can transition from an open configuration in which the aperture and an area external to the wound dressing are in fluid communication via at least one opening at a perimeter between the base layer and the top layer, to a closed configuration in which the top layer forms a seal over the aperture.

The method may further comprise connecting the base layer to the top layer via at least one supporting structure located between the base layer and the supporting layer. The method may comprise a plurality of supporting structures, as described herein. Alternatively, the method may further comprise connecting the base layer to the top layer by sealing the two layers together at one or more locations, as described herein. The sealing may be localised to one or more specific locations.

The method may comprise applying an adhesive as described herein to an upper surface of the base layer and/or a lower surface of the top layer and locating a means for providing one or more supporting structures as described herein between the top layer and the base layer.

The method may comprise producing a sheet from which a plurality of wound dressings may be cut. The sheet may be a top sheet, being a sheet made in accordance with the top layer as described herein, or a base sheet, being a sheet made in accordance with the base layer as described herein.

A top sheet may contain spaced apart islands thereon as described herein. In such an embodiment, the base sheet may be connected to the top sheet by application to the supporting structure(s). The base sheet may comprise appropriately positioned apertures. Wound dressings may be cut to a desired shape from the resulting structure.

The second and third aspects of the present invention may comprise any of the features of the first aspect of the invention as desired or as appropriate.

It is also envisaged by the present invention to provide a wound dressing comprising the top layer and the supporting structure(s), as described herein. In such a wound dressing the base layer is optional and the wound dressing could be applied directly to the wound with the supporting structure(s) connected to the patient's skin.

Thus, according to a fourth aspect of the present invention, there is provided a wound dressing comprising a wound-covering layer suitable for extending over a wound of a patient, the wound-covering layer having a wound-facing surface and a non-wound facing surface, wherein the wound-facing surface comprises at least one supporting structure for connecting the wound-covering layer to the skin of the patient in use, such that in use the wound dressing can transition from an open configuration in which the wound and an area external to the wound dressing are in fluid communication via at least one opening between a perimeter of the wound-covering layer and the patient's skin, and a closed configuration in which the wound-covering layer forms a seal over the wound.

The wound-covering layer may be, or contain any or all of the features of, the top layer as described herein in relation to the first to third aspects of the present invention.

The wound-facing surface may comprise a plurality of supporting structures. The supporting structures of the fourth aspect may be, or contain any or all of the features of, the supporting structures as described herein in relation to the first to third aspects of the present invention.

The wound dressing of the fourth aspect of the present invention may comprise any of the further features of the first aspect of the present invention as desired or as appropriate.

The wound dressing of the fourth aspect of the present invention may be applied to a patient suffering from a penetrating chest wound. The wound dressing can effectively act as a one-way valve, allowing for the flow of fluid from a patient away from the wound whilst preventing the ingress of fluid into the wound and the chest cavity. This is beneficial for assisting in the prevention of tension pneumothorax, open pneumothorax, and haemothorax and the consequences thereof. Furthermore, given the structure of the wound dressing of the present invention, it has a low profile, making it suitable and beneficial for application to a patient underneath body armour and the like.

When in the open configuration, the wound dressing of the fourth aspect may comprise an open region between the wound and the at least one opening at the perimeter. When in the closed configuration, the wound-covering layer has collapsed against the wound and around the supporting structure(s), thus substantially closing the open region between the wound and the at least one opening at the perimeter.

In the open configuration, fluid may flow around the at least one supporting structure in the open region. Where there is a plurality of supporting structures, the fluid may flow around the supporting structures in the open region.

The fourth aspect of the present invention may comprise any of the features of the first to third aspects of the invention as desired or as appropriate.

DETAILED DESCRIPTION OF THE INVENTION

Figure 2:
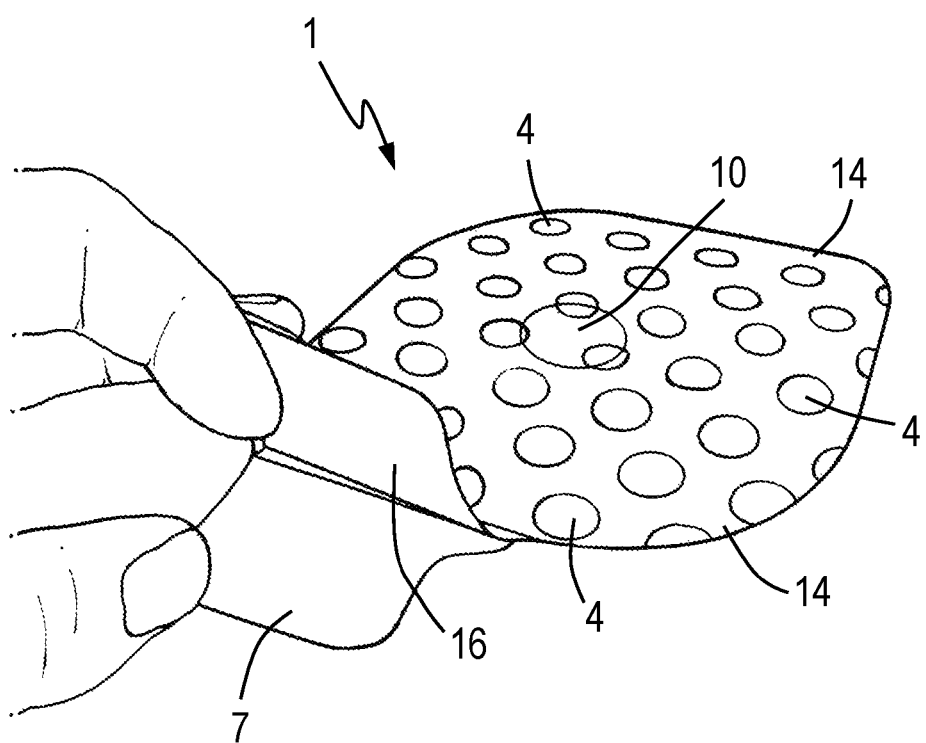
Figure 3:
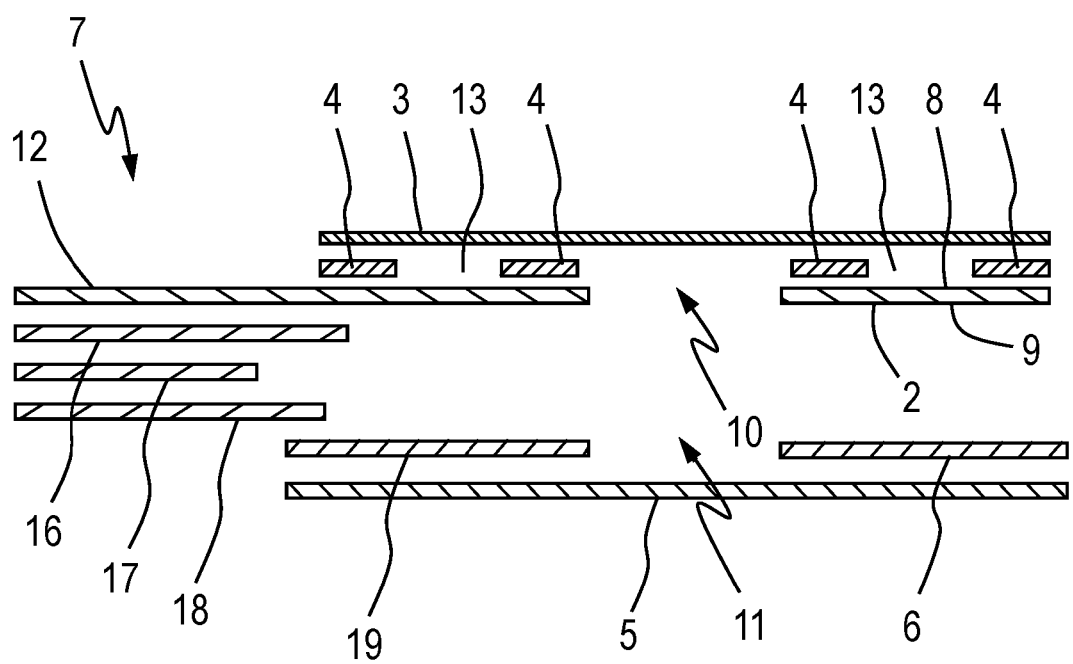
Figure 4:
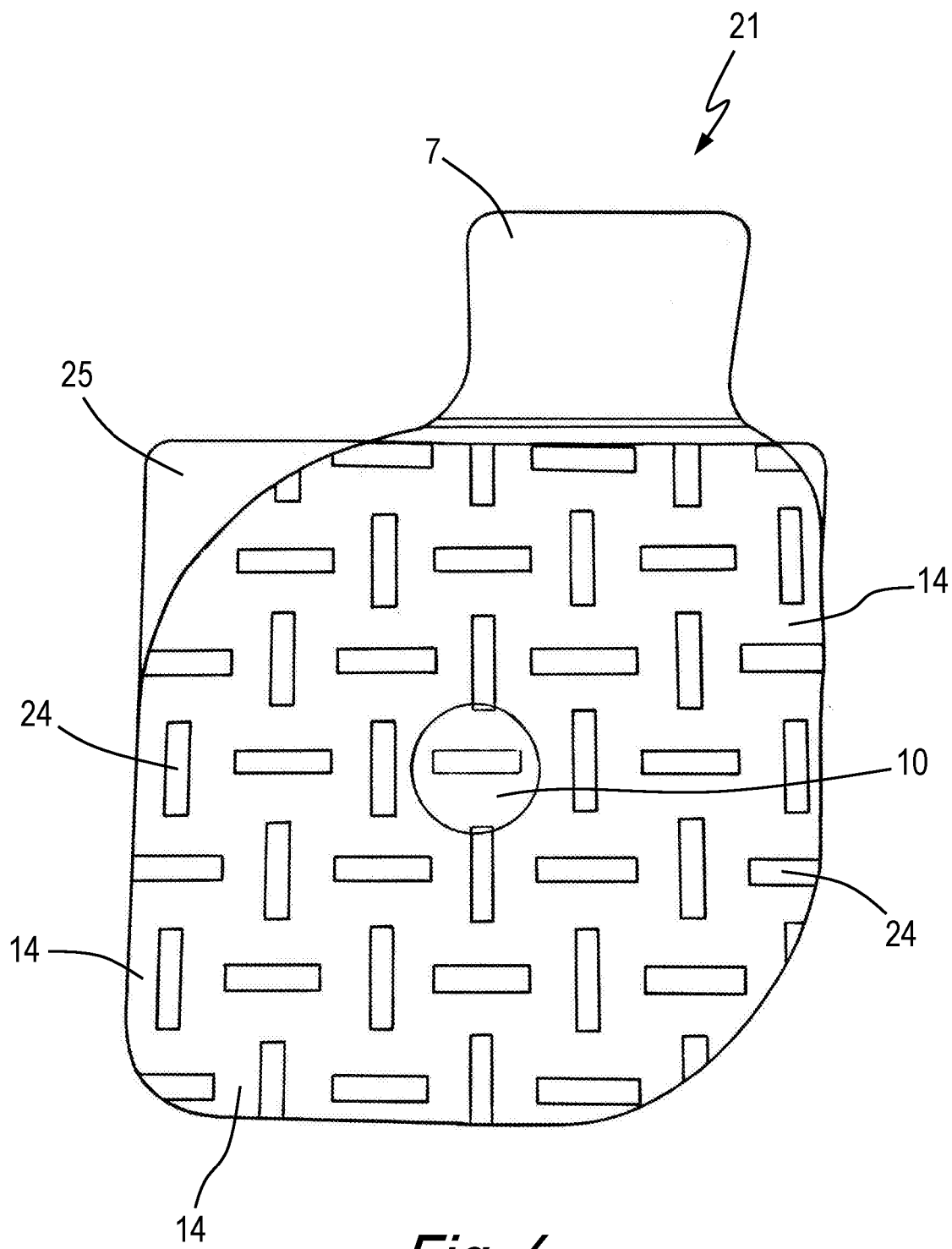

In order that the invention may be more clearly understood, an embodiment thereof will now be described, by way of example only, with reference to the accompanying drawings, of which:

FIG. 1: shows an image of a wound dressing according to the present invention;

FIG. 2: shows a further view of the wound dressing of FIG. 1;

FIG. 3: shows a cross-sectional drawing of a wound dressing of the present invention;

FIG. 4: shows an image of a further embodiment of a wound dressing according to the present invention.

Figure 5:
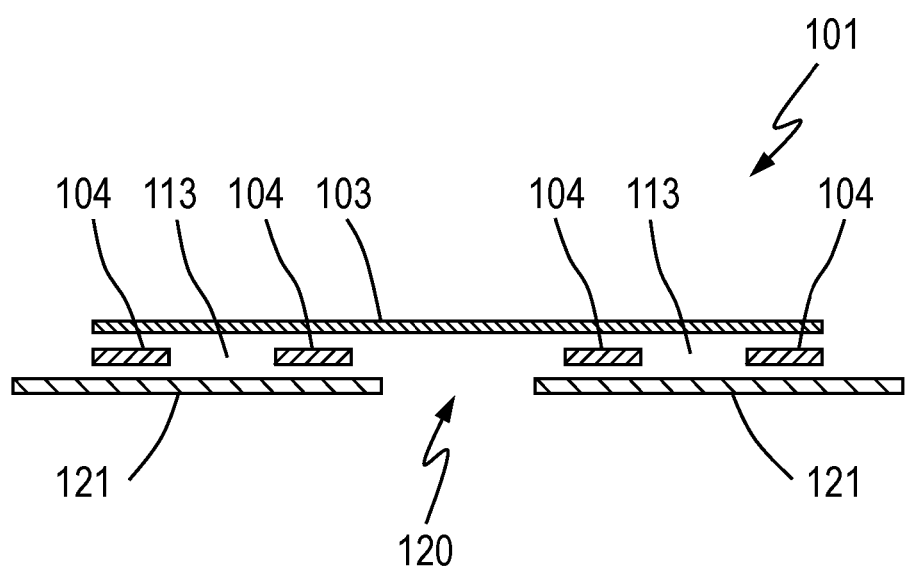

FIG. 5: shows a cross-sectional drawing of a wound dressing according to a fourth aspect of the present invention.

Figure 6:
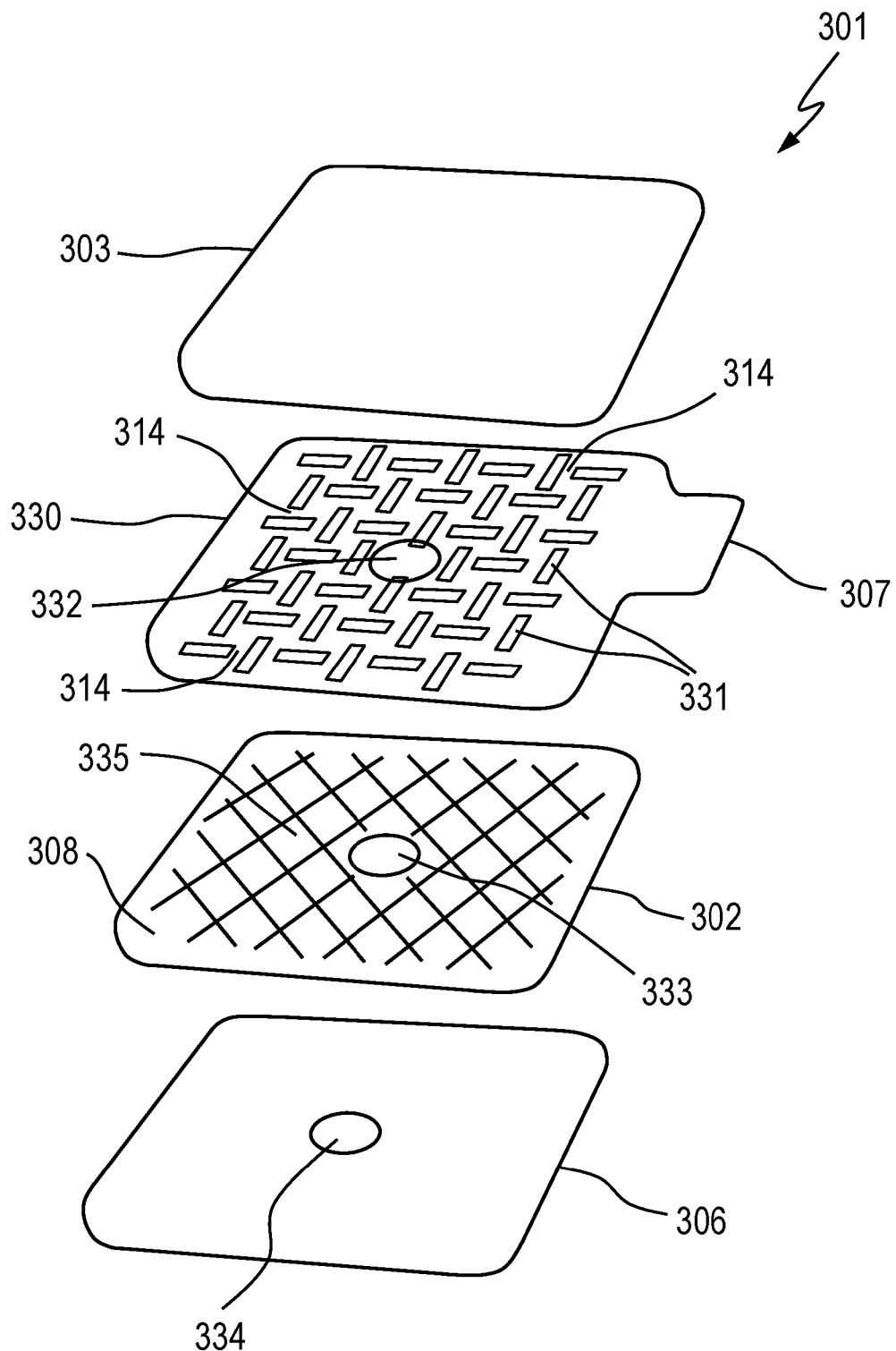

FIG. 6: shows the component layers of an alternative embodiment of the wound dressing according to the present invention.

Figure 7:
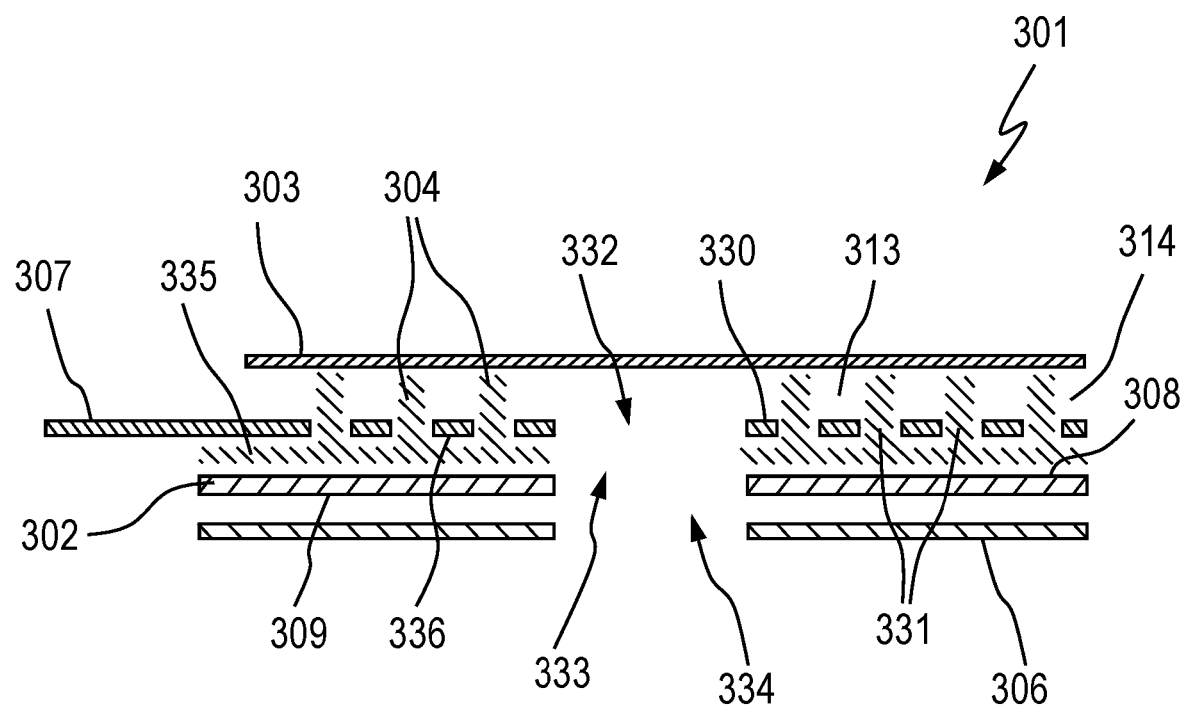

FIG. 7: shows a cross-sectional drawing of the wound dressing of FIG. 6.

Figure 8:
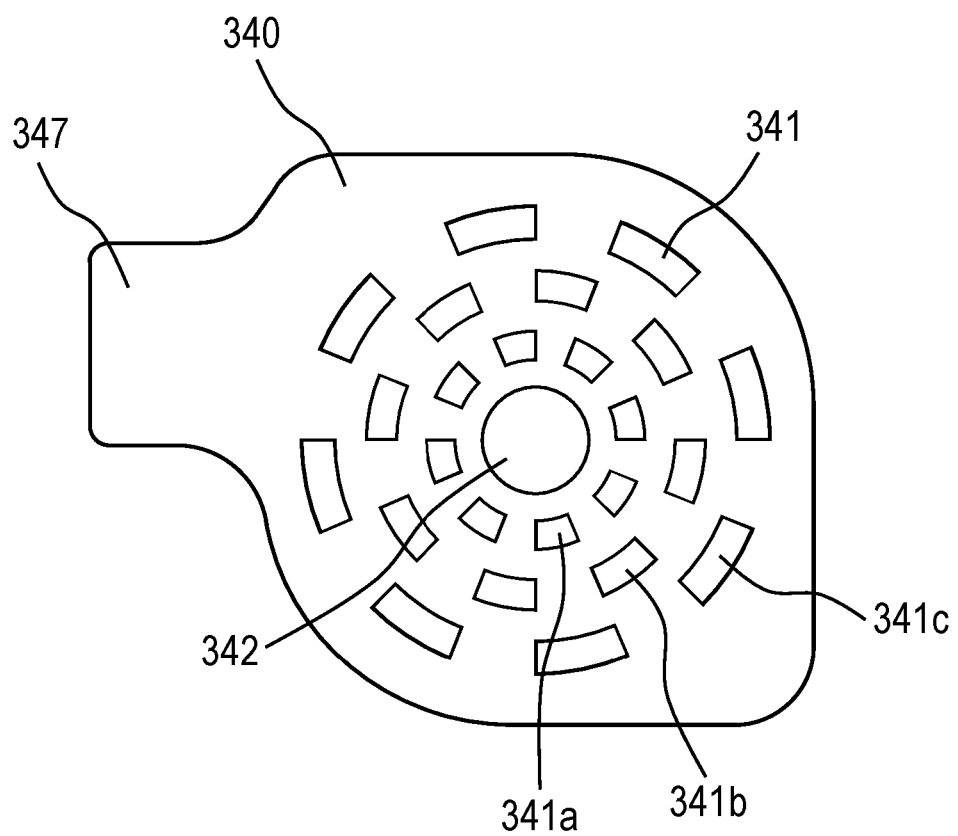

FIG. 8: shows a birds-eye view of a means for providing supporting structures according to the present invention.

A wound dressing 1 is shown in FIGS. 1 to 3 comprising a base layer 2, a top layer 3 and adhesive islands 4 connecting the top layer 3 to the base layer 2. As shown in FIG. 3, the wound dressing further comprises a removable protecting layer 5 and a skin-contact layer 6. The wound dressing 1 also comprises a tab 7.

The base layer 2 comprises an upper surface 8 which faces away from a wound and a lower surface 9 which faces toward the wound. The base layer 2 comprises an aperture 10, generally located centrally in the base layer 2.

The skin-contact layer 6 comprises an aperture 11 that corresponds to the aperture 10 located in the base layer 2. The skin-contact layer 6 is made from a hydrogel adhesive such that, once the removable protecting layer 5 is removed, it can be stuck the skin, with the wound located within the aperture 11, creating an airtight seal around the wound.

The removable protecting layer 5 is present to protect the skin-contact layer 6 prior to application to the wound and for ease of storage of the wound dressing 1.

The tab 7 comprises an extended portion 12 of the base layer 2. The tab 7 further comprises supporting layers 16, 17 and 18. The supporting layers 16, 17 and 18 provides the tab 7 with a stronger, more rigid structure which assists the user when applying the wound dressing 1. Further, the tab 7 is also useful for venting the wound dressing if required in a process known as 'burping'. The tab 7 can be lifted away from the patient's skin. Such an action raises the wound dressing 1 to provide an outlet for the release of excess pressure from the pleural cavity. The wound dressing 1 can then be resealed around the wound by applying downward pressure to the tab 7 and/or the wound dressing 1.

The top layer 3 extends over the apertures 10, 11 and to the perimeter of the base layer 2.

Between the top layer 3 and the base layer 2 are located a plurality of adhesive islands 4. The adhesive islands 4 are arranged in an ordered pattern across the surface of the base layer 2 and adhere the base layer 2 to the top layer 3. One or more of the adhesive islands 4 may overlap the aperture 10, as shown. The adhesive islands 4 have a substantially circular cross-section.

FIG. 3 shows the wound dressing 1 in an open configuration, in which an open region 13 is created between and around the adhesive islands 4. The apertures 10, 11 are in fluid communication with an area external to the wound dressing 1 via the openings 14. In use, fluid such as air and bodily fluid may flow from the apertures 10, 11, through the open region 13 and exit through the openings 14 at a perimeter between the base layer 2 and the top layer 3.

Referring to FIG. 4, there is shown a wound dressing 21 in which the adhesive islands 24 have a substantially rectangular cross-section. The wound dressing 21 also comprises a substantially rectangular removable protecting layer 25. The removable protecting layer 25 is removed prior to application of the wound dressing 21. All of the other features of the wound dressing 21 of FIG. 4 correspond to the features of the wound dressing 1 of FIGS. 1 to 3.

In use, when a human or animal suffers a penetrating chest wound, the wound dressing 1, 21 is applied over the wound. The removable protecting layer 5, 25 is removed by peeling it back to reveal the lower surface 19 of the skin-contact layer 6. The wound dressing 1, 21 is then placed over the wound, such that the apertures 10, 11 are located over the wound and encircle it. With the application of downward pressure, the skin-contact layer 6 adheres to the patient's skin surrounding the wound, creating an airtight seal.

In operation, the wound dressing 1, 21 acts as a valve to release any excessive pressure and blood build-up in the pleural cavity of the patient's lungs and therefore prevent tension pneumothorax, open pneumothorax, and haemothorax.

Once secured in place, when a patient exhales, excess pressure in the pleural cavity can force fluid to pass into apertures 10, 11 and force the top layer 3 away from the base layer 2. The top layer 3 stays connected to the base layer 2 via the adhesive islands 4. An open region 13 is formed which allows for the passing of fluid between and around the adhesive islands 4 and out into an area external to the wound dressing 1, 21 through the openings 14 at the perimeter between the base layer 2 and the top layer 3.

When a patient subsequently inhales, the pressure in the pleural cavity decreases. The decrease in pressure causes the top layer 3 to collapse against the surface of the base layer 2 and around the adhesive islands 4, 24. The collapse of the top layer 3 forms an airtight seal over the aperture 10 and closes the open region 13. In such a closed configuration, the ingress of fluid into the wound is prevented. The process will be repeated for subsequent inhalation and exhalation by the patient.

Turning to FIG. 5, there is shown a wound dressing 101, comprising a wound-covering layer 103 and adhesive islands 104.

In use, when a human or animal suffers a penetrating chest wound, the wound dressing 101 is applied over the wound 120. With the application of downward pressure, the adhesive islands 104 adhere to the patient's skin 121 surrounding the wound. In operation, the wound dressing 101 acts as a valve to release any excessive pressure and blood build-up in the pleural cavity of the patient's lungs and therefore prevent tension pneumothorax, open pneumothorax, and haemothorax.

Once secured in place, when a patient exhales, excess pressure in the pleural cavity can force fluid to force the wound-covering layer 103 away from the skin 121. The wound-covering layer 103 stays connected to the skin 121 via the adhesive islands 104. An open region 113 is formed which allows for the passing of fluid between and around the adhesive islands 104 and out into an area external to the wound dressing 101 through openings at the perimeter between the skin 121 and the wound-covering layer 103.

When a patient subsequently inhales, the pressure in the pleural cavity decreases. The decrease in pressure causes the wound-covering layer 103 to collapse against the surface of the skin 121 and around the adhesive islands 104. The collapse of the wound-covering layer 103 forms an airtight seal over the wound 120 and closes the open region 113. In such a closed configuration, the ingress of fluid into the wound is prevented. The process will be repeated for subsequent inhalation and exhalation by the patient.

Turning to FIGS. 6 and 7, there is shown a wound dressing 301 comprising a base layer 302, a top layer 303, a perforated layer 330 and a skin-contact layer 306. The perforated layer 330 comprises perforations 331 and an aperture 332. The perforated layer 330 also comprises a tab 307.

The base layer 302 comprises an upper surface 308 which faces away from a wound and a lower surface 309 which faces toward the wound. The base layer 302 comprises an aperture 333, generally located centrally in the base layer 302. The base layer 302 comprises an adhesive 335 on its upper surface.

The skin-contact layer 306 comprises an aperture 334 that corresponds to the aperture 333 located in the base layer 302. The skin-contact layer 306 is made from a hydrogel adhesive such that it can be stuck to the skin, with the wound located within the aperture 334, creating an airtight seal around the wound.

Between the top layer 303 and the base layer 302 is located the perforated layer 330.

Referring specifically to FIG. 7, there is shown a cross-section of the wound dressing 301, comprising supporting structures 304. The supporting structures 304 are provided by the perforated layer 330 enabling adhesive 335 to pass through the perforations 331 and adhere to the top layer 303. The base layer 302 is connected to the top layer 303 via the adhesive 335 being exposed to the top layer 303 through the perforations 331. The adhesive 335 also adheres the base layer 302 to a lower surface 336 of the perforated layer 330 in the positions where there are no perforations.

The tab 307 comprises an extended portion of the perforated layer 330. The tab 307 is useful for 'burping' the wound dressing 301 if required. The tab 307 can be lifted away from the patient's skin. As the base layer 302 is adhered to the perforated layer 330, such an action raises the wound dressing 301 to provide an outlet for the release of excess pressure from the pleural cavity. The wound dressing 301 can then be resealed around the wound by applying downward pressure to the tab 307 and/or the wound dressing 301.

FIG. 7 shows the wound dressing 301 in an open configuration, in which an open region 313 is created between and around the adhesive supporting structures 304. The apertures 332, 333 and 334 are in fluid communication with an area external to the wound dressing 301 via the openings 314. In use, fluid such as air and bodily fluid may flow from the apertures 332, 333, 334, through the open region 313 and exit through the openings 314 at a perimeter between the base layer 302 and the top layer 303.

In use, when a human or animal suffers a penetrating chest wound, the wound dressing 301 is applied over the wound. The wound dressing 301 is placed over the wound, such that the apertures 332, 333, 334 are located over the wound and encircle it. With the application of downward pressure, the skin-contact layer 306 adheres to the patient's skin surrounding the wound, creating an airtight seal.

In operation, the wound dressing 301 acts as a valve to release any excessive pressure and blood build-up in the pleural cavity of the patient's lungs and therefore prevent tension pneumothorax, open pneumothorax, and haemothorax.

Once secured in place, when a patient exhales, excess pressure in the pleural cavity can force fluid to pass into apertures 332, 333, 334 and force the top layer 303 away from the base layer 302. The top layer 303 stays connected to the base layer 302 via the adhesive supporting structures 304. An open region 313 is formed which allows for the passing of fluid between and around the supporting structures 304 and out into an area external to the wound dressing 301 through the openings 314 at the perimeter between the base layer 302 and the top layer 303.

When a patient subsequently inhales, the pressure in the pleural cavity decreases. The decrease in pressure causes the top layer 303 to collapse against the surface of the base layer 302 and around the adhesive supporting structures 304. The collapse of the top layer 303 forms an airtight seal over the aperture 332 and closes the open region 313. In such a closed configuration, the ingress of fluid into the wound is prevented. The process will be repeated for subsequent inhalation and exhalation by the patient.

The wound dressing of FIGS. 6 and 7 may further comprise a removable protecting layer (not shown) which can protect the skin-contact layer 306 prior to application to the wound and for ease of storage of the wound dressing 301. The removable protecting layer may be made from polyethylene terephthalate.

The wound dressing of FIGS. 6 and 7 may further comprise supporting layers (not shown) which provide the tab 307 with a stronger, more rigid structure which assists the user when applying the wound dressing 301. Further, the tab 307 is also useful for venting the wound dressing if required in a process known as 'burping'. The tab 307 can be lifted away from the patient's skin. Such an action raises the wound dressing 301 to provide an outlet for the release of excess pressure from the pleural cavity. The wound dressing 301 can then be resealed around the wound by applying downward pressure to the tab 307 and/or the wound dressing 301.

Referring to FIG. 8, there is shown a means for providing supporting structures comprising a perforated film 340. The perforated film 340 comprises perforations 341, an aperture 342 and a tab 347. The perforations 341 are provided in a pattern of three circumferential arrangements of perforations 341a, 341b, 341c that radially extend outwardly from the aperture 342. The perforations 341 are staggered, such that the perforations in the circumferential arrangement 341b are staggered relative to the perforations in the circumferential arrangements 341a and 341c. The perforated layer 340 provides supporting structures by enabling adhesive on the upper surface of a base layer or lower surface of a top layer to pass through the perforations 341 when a top layer, base layer and perforated layer 340 are brought together.

The above embodiments are described by way of example only. Many variations are possible without departing from the scope of the invention as defined in the appended claims.

The invention claimed is:

1. A wound dressing comprising:
   a base layer having a lower surface configured for facing the wound and an upper surface configured for facing away from the wound, and an aperture therethrough for locating over the wound;
   a top layer extending over the aperture and at least a part of the upper surface,
   and at least one supporting structure located between the top layer and the base layer, connecting the top layer to the base layer,
   such that the wound dressing can transition from an open configuration in which the aperture and an area external to the wound dressing are in fluid communication via at least one opening at a perimeter between the base layer and the top layer and around the at least one supporting structure, wherein the wound dressing forms a non-linear fluid path between the aperture and the external area, to a closed configuration in which the top layer has collapsed around the at least one supporting structure and forms a seal over the aperture.

2. The wound dressing as claimed in claim 1, wherein at least a portion of the upper surface of the base layer and/or the lower surface of the top layer comprises an adhesive.

3. The wound dressing as claimed in claim 2, further comprising a means for providing at least one supporting structure located between the top layer and the base layer, wherein the means for providing the at least one supporting structure comprises a perforated layer.

4. The wound dressing as claimed in claim 3, wherein the perforated layer comprises a plurality of perforations, the perforations being arranged in a radial pattern extending outwardly from the aperture.

5. The wound dressing as claimed in claim 3, wherein the at least one supporting structure is formed by adhesive passing through perforations in the perforated layer.

6. The wound dressing as claimed in claim 1, wherein the top layer is connected to the base layer by a plurality of supporting structures.

7. The wound dressing as claimed in claim 6, wherein the supporting structure comprises an island or a wall.

8. The wound dressing as claimed in claim 7, wherein the islands are spaced apart.

9. The wound dressing as claimed in claim 6, wherein the supporting structure comprises a plurality of islands.

10. The wound dressing as claimed in claim 1, further comprising a skin-contact layer attached to the lower surface of the base layer, the skin-contact layer comprising a lower surface configured for facing the wound and an upper surface configured for facing away from the wound, wherein the skin-contact layer comprises an aperture therethrough that overlaps, or corresponds to, the aperture in the base layer.

11. The wound dressing as claimed in claim 10, further comprising a removable protecting layer located on the lower surface of the skin-contact layer or the base layer.

12. The wound dressing as claimed in claim 1, further comprising an active pharmaceutical ingredient, an anticoagulant, or a combination thereof.

13. The wound dressing as claimed in claim 12, further comprising:
   a means for providing at least one supporting structure located between the top layer and the base layer, wherein the means for providing the at least one supporting structure comprises a perforated layer;
   a skin-contact layer attached to the lower surface of the base layer, the skin-contact layer comprising a lower surface configured for facing the wound and an upper surface configured for facing away from the wound, wherein the skin-contact layer comprises an aperture therethrough that overlaps, or corresponds to, the aperture in the base layer; and a tab,
   wherein the active pharmaceutical ingredient, the anticoagulant, or the combination thereof are at least partially coated onto, or contained in, any one or more of the top layer, the base layer, the means for providing one or more supporting structures, the skin-contact layer, the at least one supporting structure(s), and the tab.

14. The wound dressing as claimed in claim 1, wherein the supporting structure is made from an adhesive material.

15. The wound dressing as claimed in claim 1, wherein the supporting structure overlaps at least a portion of the aperture.

16. The wound dressing as claimed in claim 1, wherein the perimeter between the base layer and the top layer comprises a plurality of openings.

17. The wound dressing as claimed in claim 1, wherein the at least a portion of the lower surface of the base layer comprises an adhesive.

18. The wound dressing as claimed in claim 1, further comprising a tab.

19. The wound dressing as claimed in claim 1, wherein the wound dressing is applied to a penetrating chest wound.

20. A wound dressing comprising a wound-covering layer suitable for extending over a wound of a patient, the wound-covering layer having a wound-facing surface and a non-wound facing surface, wherein the wound-facing surface comprises at least one supporting structure for connecting the wound-covering layer to the skin of the patient in use, such that in use the wound dressing can transition from an open configuration in which the wound and an area external to the wound dressing are in fluid communication via at least one opening configured to be between a perimeter of the wound-covering layer and skin of the patient and around the at least one supporting structure, wherein the wound dressing forms a non-linear fluid path between the aperture and the external area, and a closed configuration in which the wound-covering layer has collapsed around the at least one supporting structure and forms a seal over the wound.

21. The wound dressing as claimed in claim 20, further comprising an active pharmaceutical ingredient, an anticoagulant, or a combination thereof.

22. The wound dressing as claimed in claim 21, wherein the wound covering layer and/or the at least one supporting structure is at least partially coated with, or contains, the active pharmaceutical ingredient, the anticoagulant, or combination thereof.

23. A method of manufacturing a wound dressing, comprising connecting a base layer having a lower surface configured for facing the wound and an upper surface configured for facing away from the wound, and an aperture therethrough for locating over the wound, a top layer extending over the aperture and at least a part of the upper surface, and at least one supporting structure located between the top layer and the base layer, connecting the top layer to the base layer, such that the wound dressing can transition from an open configuration in which the aperture and an area external to the wound dressing are in fluid communication via at least one opening at a perimeter between the base layer and the top layer and around the at least one supporting structure, wherein the wound dressing forms a non-linear fluid path between the aperture and the external area, to a closed configuration in which the top layer has collapsed around the at least one supporting structure and forms a seal over the aperture.

24. The method as claimed in claim 23, wherein the base layer is connected to the top layer via at least one supporting structure located between the base layer and the supporting layer.

* * * * *